US 6,610,748 B1

(12) United States Patent
Yabuta et al.

(10) Patent No.: US 6,610,748 B1
(45) Date of Patent: Aug. 26, 2003

(54) PREVENTIVES/REMEDIES FOR SKIN AGING

(75) Inventors: Tsuguo Yabuta, Ibaraki (JP); Mitsuru Yasumura, Nishinomiya (JP); Kunio Nakahara, Hyogo (JP); Yusuke Furukawa, Nara (JP); Kazuhiko Nomura, Ibaraki (JP); Manabu Murakami, Suita (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/622,053

(22) PCT Filed: Feb. 19, 1999

(86) PCT No.: PCT/JP99/00761

§ 371 (c)(1),
(2), (4) Date: Dec. 15, 2000

(87) PCT Pub. No.: WO99/43352

PCT Pub. Date: Sep. 2, 1999

(30) Foreign Application Priority Data

Feb. 24, 1998 (JP) ............................................... 10/41479

(51) Int. Cl.⁷ ..................... A01N 37/18; A01N 43/36; A01N 35/00
(52) U.S. Cl. ..................... 514/621; 514/613; 514/408; 514/675
(58) Field of Search ................................. 424/117, 118; 514/18, 408, 613, 621, 675; 530/331

(56) References Cited

U.S. PATENT DOCUMENTS

| | | | | | |
|---|---|---|---|---|---|
| 5,021,240 A | * | 6/1991 | Hatanaka et al. | ............ | 424/118 |
| 5,167,958 A | * | 12/1992 | Hatanaka et al. | ............ | 424/118 |
| 5,279,826 A | * | 1/1994 | Inamura et al. | ............. | 424/117 |
| 5,292,510 A | * | 3/1994 | Takase et al. | ............... | 424/117 |
| 5,296,591 A | * | 3/1994 | Hemmi et al. | .............. | 530/331 |
| 5,364,624 A | * | 11/1994 | Takase et al. | ............... | 424/117 |
| 5,565,429 A | * | 10/1996 | Vincent et al. | ............... | 514/18 |
| 5,567,804 A | * | 10/1996 | de Nanteuil et al. | ........ | 530/331 |
| 5,618,792 A | * | 4/1997 | Gyorkos et al. | .............. | 514/18 |

OTHER PUBLICATIONS

H. Roenigk, Jr., et al "Skin Manifestation of Psoriasis From "Psoriasis"", $2^{nd}$ edition, Marcel Dekker, Pubs., pp. 3–8, 1990.

M. Tan et al., "Psoriasis", From "Drugs of Today", 1998, vol. 34, Issue 7, pp. 641–647.

L. Kemeny et al., "Cytokine system as potential target for antipsoriatic therapy", Exp Dermatol, 1994, pp. 1–8.

A. Kapp, "The role of cytokines in the psoriatic inflammation", Journal of Dermatological Science, 1993, p. 1.

B. Baker et al., "The Immunology of psoriasis", British Journal of Dermatology, 1992, pp. 1–9.

* cited by examiner

Primary Examiner—Sreeni Padmanabhan
Assistant Examiner—Michael A. Willis
(74) Attorney, Agent, or Firm—Oblon, Spivak, McClelland, Maier & Neustadt, P.C.

(57) ABSTRACT

A composition for prophylaxis and therapy of dermal aging which comprises a substance having human leukocyte elastase inhibitory activity as an active ingredient.

5 Claims, No Drawings

PREVENTIVES/REMEDIES FOR SKIN AGING

This is a 371 of PCT/JP99/00761, filed Feb. 19, 1999.

TECHNICAL FIELD

This invention relates to a composition for prophylaxis and therapy of dermal aging which comprises a substance having human leukocyte elastase inhibitory activity as an active ingredient.

BACKGROUND ART

Aging of the skin is said to begin after the third decade of life. Obvious signs of aging include decreases in the moisture, gloss, smoothness, tonus, etc. of the skin and an increased number of wrinkles. These are suspected to result from the morphological and functional changes of the organs and tissues making up the skin. Thus, aging is accompanied by thinning of the epidermis and loss of oxytalan fiber in the papillary layer of the dermis.

Dermal aging, epitomized by wrinkling of the skin, is a serious beauty problem for women but no satisfactory remedy has been available to this day.

The present inventors discovered that a substance having human leukocyte elastase inhibitory activity is effective in the prevention and treatment of dermal aging and has perfected this invention.

DISCLOSURE OF INVENTION

This invention is directed to a composition for prophylaxis and therapy of dermal aging which comprises a substance having human leukocyte elastase inhibitory activity as an active ingredient.

The substance having human leukocyte elastase inhibitory activity which can be used as the active ingredient of this composition for prophylaxis and therapy of dermal aging may be any substance that has human leukocyte elastase inhibitory activity. Furthermore, the substance having human leukocyte elastase activity which can be used in this invention includes not only substances which are direct inhibitors of that activity but also substances which inhibit leukocyte elastase activity indirectly through suppression of leukocyte infiltration and inhibition of elastase production. Thus, while many substances having such activity are known, any novel substance that may have human leukocyte elastase inhibitory activity can also be employed. The following is a partial listing of the preferred compounds in this category.

(1) WS7622A mono- or disulfate and pharmaceutically acceptable salts thereof; among these, WS7622A disulfate ester disodium salt and WS7622A disulfate ester dipotassium salt are known substances which have the following physicochemical properties (JP Kokai H4-279600).

WS7622A disulfate ester disodium salt (hereinafter sometimes referred to briefly as FR134043):

Description: Colorless crystals
Solubility: Soluble: water, methanol
Insoluble: chloroform, n-hexane
Melting point: 257~263° C. (decomp.)
Optical rotation: $[\alpha]^{23}_D$ +37.5° (c=1, methanol)
Molecular formula: $C_{47}H_{61}N_9O_{19}S_2Na_2$
Elemental analysis: Calcd.: (for $C_{47}H_{61}N_9O_{19}S_2Na_2 \cdot 6H_2O$): C, 44.30; H, 5.77; N, 9.89; S, 5.03; Na, 3.61%; Found: C, 44.98; H, 5.90; N, 10.06; S, 5.00; Na, 3.98%; Molecular weight: FAB-MS m/z 1188 $(M+Na)^+$ Thin-layer chromatography:

TABLE 1

| Stationary phase | Developer solvent | Rf |
|---|---|---|
| Silica gel (Merck Art. 5715) | $CHCl_3$—$CH_3OH$—$H_2O$ (65:25:4) | 0.11 |
| | n-butanol-acetic acid-water (4:2:1) | 0.29 |

$^1$H Nuclear magnetic resonance spectrum:

| (400 MHz, $D_2O$)δ: | |
|---|---|
| 7.50 | (1H, s) |
| 7.27 | (1H, s) |
| 7.33–7.24 | (3H, m) |
| 6.94 | (1H, q, J = 7 Hz) |
| 6.85 | (2H, br d, J = 8 Hz) |
| 5.53 | (1H, m) |
| 5.37 | (1H, m) |
| 4.80 | (1H, br s) |
| 4.63–4.57 | (2H, m) |
| 4.53 | (1H, m) |
| 4.06 | (1H, m) |
| 3.99 | (1H, d, J = 10 Hz) |
| 3.56 | (1H, br d, J = 14 Hz) |
| 3.46 | (1H, m) |
| 2.97 | (3H, s) |
| 2.97–2.88 | (2H, m) |
| 2.72 | (1H, m) |
| 2.59 | (1H, m) |
| 2.51–2.38 | (2H, m) |
| 2.09–1.91 | (4H, m) |
| 1.82–1.60 | (3H, m) |
| 1.77 | (3H, d, J = 7 Hz) |
| 1.50 | (3H, d, J = 6.5 Hz) |
| 1.40 | (1H, m) |
| 1.11 | (6H, d, J = 7 Hz) |
| 0.99 | (3H, d, J = 6.5 Hz) |
| 0.97 | (3H, d, J = 6.5 Hz) |

$^{13}$C Nuclear magnetic resonance spectrum:

| (100 MHz, $D_2O$)δ | |
|---|---|
| 183.6 | (s) |
| 177.9 | (s) |
| 177.7 | (s) |
| 174.8 | (s) |
| 173.8 | (s) |
| 173.3 | (s) |
| 172.4 | (s) |
| 167.8 | (s) |
| 161.5 | (s) |
| 145.5 | (s) |
| 144.9 | (s) |
| 139.6 | (d) |
| 139.0 | (s) |
| 137.0 | (s) |
| 136.0 | (s) |
| 132.3 | (d) × 2 |
| 131.0 | (d) × 2 |
| 129.6 | (d) |
| 127.4 | (d) |
| 125.9 | (d) |
| 77.4 | (d) |
| 75.1 | (d) |
| 63.8 | (d) |
| 62.7 | (d) |
| 59.1 | (d) |

-continued

| (100 MHz, $D_2O$)δ | |
|---|---|
| 55.9 | (d) |
| 54.9 | (d) |
| 51.9 | (d) |
| 41.9 | (t) |
| 37.2 | (d) |
| 36.9 | (t) |
| 34.1 | (q) |
| 32.3 | (d) |
| 31.9 | (t) |
| 31.8 | (t) |
| 31.2 | (t) |
| 27.5 | (t) |
| 23.7 | (t) |
| 21.7 | (q) |
| 21.4 | (q) × 2 |
| 21.3 | (q) |
| 21.1 | (q) |
| 15.5 | (q) |

Amino Acid Analysis:

WS7622A disulfate ester disodium salt (1 mg) was hydrolyzed with 6 N-hydrochloric acid at 110° C. for 20 hours and, then, concentrated to dryness under reduced pressure, and the residue was analyzed with Hitachi 835 Automatic Amino Acid Analyzer. As the amino acids standard solution, Wako Pure Chemical's Type H (Wako Code 013-08391) and Type B (016-08641) were used.

As a result, threonine, valine, phenylalanine, ornithine, ammonia and several unknown ninhydrin-positive components were detected.

As a partial chemical structure of WS7622A disulfate ester disodium salt, the following formula is proposed.

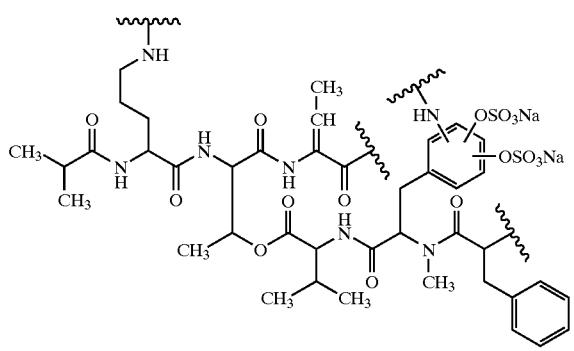

WS7622A disulfate ester dipotassium salt:

Description: Colorless amorphous powders

Solubility: Soluble: water, methanol

Insoluble: chloroform, n-hexane

Melting point: 230~237° C. (decomp.)

Optical rotation: $[\alpha]^{23}_D$ +34° (c=1, methanol)

Molecular formula: $C_{47}H_{61}N_9O_{19}S_2K_2$

Elemental analysis: Calcd.: (for $C_{47}H_{61}N_9O_{19}S_2K_2 \cdot 6H_2O$): C, 43.21; H, 5.63; N, 9.65; S, 7.91; Na, 5.99%; Found: C, 43.96; H, 5.44; N, 9.97; S, 5.09; Na, 4.49%; Molecular weight: FAB-MS m/z 1236 (M+K)$^+$ Thin-layer chromatography:

TABLE 2

| Stationary phase | Developer solvent | Rf |
|---|---|---|
| Silica gel (Merck Art. 5715) | $CHCl_3$—$CH_3OH$—$H_2O$ | 0.13 |

Infrared absorption spectrum: $\nu^{KBr}_{max}$: 3360, 2960, 1735, 1660, 1640, 1530, 1500, 1405, 1380, 1250, 1200, 1050, 1030, 940, 890 cm$^{-1}$ ;

$^1$H Nuclear magnetic resonance spectrum:

| (400 MHz, $D_2O$)δ: | |
|---|---|
| 7.52 | (1H, s) |
| 7.28 | (1H, s) |
| 7.34–7.25 | (3H, m) |
| 6.96 | (1H, q, J = 7 Hz) |
| 6.87 | (2H, br d, J = 8 Hz) |
| 5.56 | (1H, m) |
| 5.40 | (1H, m) |
| 4.84 | (1H, br s) |
| 4.70–4.55 | (3H, m) |
| 4.10 | (1H, m) |
| 4.03 | (1H, m) |
| 3.60 | (1H, br d, J = 14 Hz) |
| 3.50 | (1H, m) |
| 3.00 | (3H, s) |
| 3.00–2.85 | (2H, m) |
| 2.76 | (1H, m) |
| 2.62 | (1H, m) |
| 2.55–2.40 | (2H, m) |
| 2.12–1.95 | (4H, m) |
| 1.90–1.65 | (3H, m) |
| 1.79 | (3H, d, J = 7 Hz) |
| 1.53 | (3H, d, J = 6.5 Hz) |
| 1.45 | (1H, m) |
| 1.14 | (6H, d, J = 7 Hz) |
| 1.02 | (3H, d, J = 6.5 Hz) |
| 1.00 | (3H, d, J = 6.5 Hz) |

Amino Acid Analysis:

WS7622A disulfate ester dipotassium salt (1 mg) was hydrolyzed with 6 N-hydrochloric acid (1 ml) at 110° C. for 20 hours and, then, concentrated to dryness under reduced pressure, and the residue was analyzed with Hitachi 835 Automatic Amino Acid Analyzer. As the amino acids standard solution, Wako Pure Chemical's Type H (Wako Code 013-08391) and Type B (016-08641) were used.

As a result, threonine, valine, phenylalanine, ornithine, ammonia and several unknown ninhydrin-positive components were detected.

As a partial chemical structure of WS7622A disulfate ester dipotassium salt, the following formula is proposed.

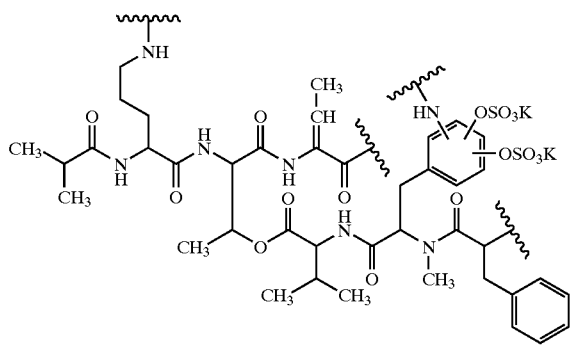

As the pharmaceutically acceptable salt of WS7622A mono- or disulfate ester, there can be mentioned the mono- or di-salts with inorganic or organic bases, such as alkali metal salts (e.g. sodium salt, potassium salt, etc.), alkaline earth metal salts (e.g. calcium salt etc.), ammonium salt, ethanolamine salt, triethylamine salt, dicyclohexylamine salt and pyridine salt, among others.

Substance WS7622A which is a starting compound for synthesis of said WS7622A mono- or disulfate ester also has human leukocyte elastase inhibitory activity and can, therefore, be used as a prophylactic and therapeutic agent for wrinkles. This substance is known to have the following physicochemical properties (JP Kokai H3-218387, JP Kokai H4-279600).

Physicochemical properties of Substance WS7622A:

Description: colorless prisms

Acidity-alkalinity: acidic

Color reactions:
  Positive: cerium sulfate reaction, iodine vapor reaction, ferric chloride reaction
  Negative: ninhydrin reaction, Molisch reaction, Dragendorff reaction Solubility:
  Soluble: methanol, ethanol, n-butanol
  Slightly soluble: chloroform, acetone, ethyl acetate
  Insoluble: water, n-hexane Thin-layer chromatography (TLC):
  Chloroform-methanol (5:1, v/v) Rf 0.51
  Acetone-methanol (10:1) Rf 0.62
  (Kieselgel 60$F_{254}$ silica gel plate, Merck).

Melting point: 250–252° C. (decomp.); Optical rotation: $[\alpha]^{23}_D$ +36° (c=1, methanol); UV absorption spectrum: $\lambda^{MeOH}_{max}$ 287 nm ($\epsilon$=3600) $\lambda^{MeOH-Hcl}_{max}$ 287 nm $\lambda^{MeOH-NaOH}_{max}$ 298 nm; Molecular formula: $C_{47}H_{63}N_9O_{13}$; Elemental analysis: Calcd.: (for $C_{47}H_{63}N_9O_{13}·2H_2O$): C, 56.56; H, 6.77; N, 12.63%; Found: C, 56.65; H, 6.62, N, 12.27%; Molecular weight: FAB-MS m/z 984 (M+Na)$^+$;

Infrared absorption spectrum: $\epsilon^{KBr}_{max}$: 3400, 3300, 3060, 2980, 2940, 1735, 1710, 1690, 1670, 1660, 1640, 1540, 1520, 1470, 1380, 1330, 1300, 1260, 1220, 1200, 1160, 1130, 1090, 1000, 980, 940, 920 cm$^{-1}$; $^1$H Nuclear magnetic resonance spectrum: (400 MHz, CD$_3$OD)δ:

| | |
|---|---|
| 7.22–7.09 | (3H, m) |
| 6.88–6.77 | (3H, m) |
| 6.74 | (1H, s) |
| 6.46 | (1H, s) |
| 5.46 | (1H, m) |
| 5.18 | (1H, s) |
| 4.85 | (1H, s) |
| 4.77 | (1H, m) |
| 4.65 | (1H, m) |
| 4.50 | (1H, m) |
| 3.96 | (1H, m) |
| 3.91 | (1H, d, J = 9 Hz) |
| 3.60–3.47 | (2H, m) |
| 3.03 | (1H, m) |
| 2.90 | (3H, s) |
| 2.86 | (1H, m) |
| 2.59–2.49 | (2H, m) |
| 2.39 | (1H, m) |
| 2.29–2.16 | (2H, m) |
| 2.00 | (1H, m) |
| 1.84 | (1H, m) |
| 1.74 | (3H, d, J = 6 Hz) |
| 1.72–1.53 | (4H, m) |
| 1.44 | (3H, d, J = 6 Hz) |
| 1.12 | (1H, m) |
| 1.10 | (6H, d, J = 6 Hz) |
| 0.99 | (3H, d, J = 6 Hz) |
| 0.94 | (3H, d, J = 6 Hz) |

$^{13}$C Nuclear magnetic resonance spectrum:

| (100 MHz, CD$_3$OD)δ | |
|---|---|
| 179.7 | (s) |
| 176.3 | (s) |
| 174.7 | (s) |
| 173.3 | (s) |
| 172.4 | (s) |
| 171.4 | (s) |
| 170.3 | (s) |
| 165.8 | (s) |
| 160.2 | (s) |
| 145.7 | (s) |
| 145.6 | (s) |
| 137.5 | (s) |
| 134.0 | (d) |
| 131.4 | (s) |
| 130.6 | (d) × 2 |
| 129.8 | (s) |
| 129.1 | (d) × 2 |
| 129.1 | (s) |
| 127.6 | (d) |
| 119.1 | (d) |
| 118.0 | (d) |
| 76.0 | (d) |
| 73.4 | (d) |
| 63.1 | (d) |
| 61.4 | (d) |
| 57.1 | (d) |
| 53.6 | (d) |
| 52.7 | (d) |
| 50.5 | (d) |
| 39.9 | (t) |
| 36.1 | (t) |
| 35.8 | (d) |
| 31.8 | (q) |
| 31.0 | (t) |
| 30.8 | (d) |
| 29.9 | (t) |
| 29.7 | (t) |
| 25.2 | (t) |
| 22.3 | (t) |
| 20.2 | (q) |
| 20.0 | (q) × 2 |
| 19.7 | (q) |
| 19.5 | (q) |
| 13.3 | (q) |

Amino Acid Analysis:
WS7622A (1 mg) was hydrolyzed with 6 N-hydrochloric acid (1 m) at 110° C. for 20 hours and concentrated to dryness under reduced pressure, and the residue was analyzed with Hitachi 835 Automatic Amino Acid Analyzer. As the amino acids standard solution, Wako Pure Chemical's Type H (Wako Code 013-08391) and Type B (016-08641) were used.

As a result, threonine, valine, phenylalanine, ornithine, ammonia and several unknown ninhydrin-positive components were detected.

As a partial chemical structure of WS7622A, the following formula is proposed.

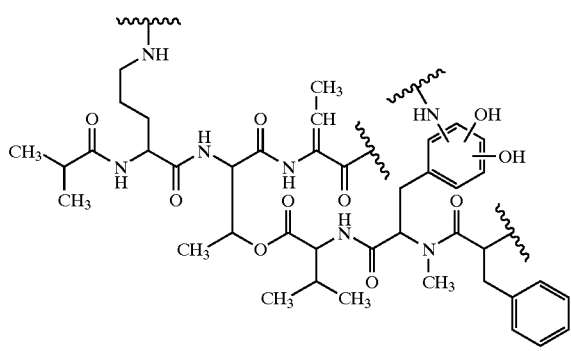

The salt of Substance WS7622A includes salts with inorganic or organic bases, such as alkali metal salts (e.g. sodium salt, potassium salt, etc.), alkaline earth metal salts (e.g. calcium salt etc.), ammonium salt, ethanolamine salt, triethylamine salt and dicyclohexylamine salt, among others.

Substances WS7622B, C and D and derivatives thereof (JP Kokai H3-218387), all of which have human leukocyte elastase inhibitory activity as well can also be used as prophylactic and therapeutic agents for wrinkles.

The above-mentioned Substance WS7622A (as well as Substances WS7622B, C and D) can be produced by growing *Streptomyces resistomycificus* No. 7622, which strain has been deposited with National Institute of Bioscience and Human Technology, one of the international culture collections under Budapest Treaty, with the accession number of FERM BP-2306 assigned.

(2) A trifluoromethylketone derivative of the following formula and its pharmaceutically acceptable salt:

[wherein $R^1$ represents a lower alkyl group having 1 or 2 substituents selected from among carboxy, esterified carboxy and di-lower alkylcarbamoyl; a phenyl(lower)alkyl group which may optionally have halogen, amino or nitro on the phenyl moiety thereof and carboxy or esterified carboxy on the alkyl moiety thereof; a halophenyl group; a morpholino group; or a morpholino (lower) alkyl group; $R^2$ and $R^3$ each represents a lower alkyl group; X represents — or —NH—;

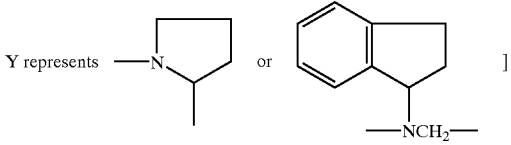

(3) a trifluoromethylketone derivative of the following formula and its pharmaceutically acceptable salt:

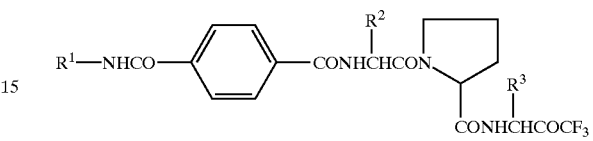

(wherein $R^1$~$R^3$ have the same meanings as defined above (2)).

(4) 3 (RS)-[[4-(carboxymethylaminocarbonyl)phenylcarbonyl]-L-valyl-L-prolyl]amino-1,1,1-trifluoro-4-methyl-2-oxopentane or its sodium salt (this sodium salt will sometimes be referred to briefly as FK706).

The compounds mentioned in the above paragraphs (2)~(4) are known compounds as described in JP Kokai H4-297446, for instance. As the pharmaceutically acceptable salts of said compounds (2)~(3), there can be mentioned the respective salts with organic or inorganic bases, such as alkali metal salts (e.g. sodium salts, potassium salts, etc.), alkaline earth metal salts (e.g. calcium salts etc.), ammonium salts, ethanolamine salts, triethylamine salts, dicyclohexylamine salts, etc., methanesulfonates, and organic or inorganic acid addition salts such as hydrochlorides, sulfates, nitrates, phosphates and so forth.

The preferred examples relevant to the various definitions given hereinbefore are now set forth in detail. The term "lower" means 1~6 carbon atoms unless otherwise specified. As the preferred examples of "halogen", there can be mentioned fluoro, chloro, bromo and iodo. The preferred "lower alkyl group" includes residues of straight-chain or branched-chain alkanes containing 1~6 carbon atoms, such as methyl, ethyl, propyl, isopropyl, butyl, isobutyl, t-butyl, pentyl, neopentyl and hexyl, preferably those having 1~4 carbon atoms. The preferred "esterified carboxy" includes, among others, alkyl esters, i.e. alkoxycarbonyl groups such as lower alkoxycarbonyl (e.g. methoxycarbonyl, ethoxycarbonyl, propoxycarbonyl, butoxycarbonyl, tert-butoxycarbonyl, etc.), and phenyl(lower)alkyl esters, i.e. phenyl(lower)alkoxycarbonyl groups such as benzyloxycarbonyl etc., and benzoyl(lower)alkyl esters, i.e. benzoyl(lower)alkoxycarbonyl groups such as benzoylmethoxycarbonyl and so forth.

The preferred "lower alkylene group" includes but is not limited to methylene, ethylene, propylene and isopropylene. The preferred "di-lower-alkylcarbamoyl group" includes N,N-dimethylcarbamoyl and N,N-diethylcarbamoyl, among others.

(5) Substance FR901451 having the following physicochemical properties and its pharmaceutically acceptable salt:

Description: white powders
Color reactions:
  Positive: cerium sulfate, iodine vapor, Ehrlich, and ninhydrin reactions Negative: Molisch reaction Solubility:
  Soluble: water, methanol, dimethyl sulfoxide
  Hardly soluble: acetate
  Insoluble: ethyl acetate Melting point: 243~245° C. (decomp.); Optical rotation: $[\alpha]^{23}_D$ -15° (c=0.65, H$_2$O); Ultraviolet absorption spectrum: $\lambda^{MeOH}_{max}$ nm ($\epsilon$): 275 (4300), 281 (4500), 290 (3900); Molecular formula: $C_{60}H_{79}N_{13}O_{18}$; Elemental analysis: Calcd.: (for $C_{60}H_{79}N_{13}O_{18} \cdot 10_2$): C, 49.68; H, 6.88; N, 12.55; Found: C, 49.95; H, 6.28; N, 12.42; Molecular weight: FAB-MS m/z 1270 (M+H)$^+$; Thin-layer chromatography:

TABLE 3

| Stationary phase | Developer solvent | Rf |
|---|---|---|
| Silica gel (Merck) | CHCl$_3$:MeOH:NH$_4$OH (15:11:5) | 0.60 |
| RP-18 (Merck) | 70% aqueous methanol | 0.32 |

FT-IR spectrum: $\epsilon^{KBr}_{max}$: 3390, 3070, 2970, 2880, 1740, 1660, 1530, 1450, 1410, 1380, 1350, 1250, 1190, 1110, 1080, 1010, 750, 700, 670, 660, 620, 600 cm$^{-1}$;

$^1$H Nuclear magnetic resonance spectrum:

(400 MHz, D$_2$O)δ:

| | |
|---|---|
| 7.70 | (1H, d, J = 7 Hz) |
| 7.52 | (1H, d, J = 7.5 Hz) |
| 7.44–7.23 | (7H, m) |
| 7.22 | (1H, s) |
| 5.59 | (1H, q, J = 7 Hz) |
| 4.94 | (1H, t, J = 4.5 Hz) |
| 4.85–4.74 | (3H, m) |
| 4.58 | (1H, dd, J = 6 Hz, 10 Hz) |
| 4.45–4.35 | (3H, m) |
| 4.30 | (1H, dd, J = 4 Hz, 7 Hz) |
| 4.07 | (1H, m) |
| 3.99 | (1H, dd, J = 10 Hz, 4.5 Hz) |
| 3.66–3.50 | (3H, m) |
| 3.44–3.25 | (4H, m) |
| 3.16–2.93 | (4H, m) |
| 2.87 | (1H, d, J = 18 Hz) |
| 2.80–2.68 | (2H, m) |
| 2.56–2.48 | (2H, m) |
| 2.08 | (1H, dd, J = 16 Hz, 4 Hz) |
| 1.87–1.53 | (9H, m) |
| 1.43 | (3H, d, J = 7 Hz) |
| 1.30 | (3H, d, J = 6.5 Hz) |
| 1.45–1.17 | (4H, m) |
| 0.95 | (3H, d, J = 6 Hz) |
| 0.84 | (3H, d, J = 6 Hz) |

$^{13}$C Nuclear magnetic resonance spectrum:

(100 MHz, D$_2$O)δ

| | | | |
|---|---|---|---|
| 177.2 (s) | 130.0 (d) × 2 | 56.0 (d) | 31.4 (t) |
| 176.5 (s) | 129.8 (d) × 2 | 54.1 (d) | 28.8 (t) |
| 174.6 (s) | 128.5 (d) | 53.8 (d) | 26.6 (t) |
| 174.2 (s) | 127.8 (d) | 53.2 (d) | 25.1 (d) |
| 174.0 (s) | 125.5 (d) | 53.1 (d) | 23.2 (q) |
| 173.2 (s) | 123.2 (d) | 52.9 (d) | 23.2 (t) |
| 173.0 (s) | 120.9 (d) | 52.8 (d) | 23.1 (t) |
| 172.8 (s) | 118.7 (d) | 49.5 (d) | 20.8 (q) |
| 172.6 (s) | 113.1 (d) | 48.6 (t) | 19.4 (q) |
| 172.5 (s) | 108.8 (s) | 40.1 (t) | 18.3 (q) |
| 172.1 (s) | 73.3 (d) | 39.6 (t) | |
| 171.7 (s) | 69.7 (d) | 39.4 (t) | |
| 171.4 (s) | 64.3 (t) | 38.9 (t) | |
| 170.3 (s) | 62.1 (d) | 35.3 (t) | |
| 137.2 (s) | 60.9 (d) | 34.8 (t) | |
| 136.0 (s) | 57.1 (d) | 31.7 (t) | |

The above Substance FR901451 is known as the substance elaborated by Substance FR901451-producing strains of organisms belonging to the genus Flexibacter (e.g. WO93/02203). Flexibacter sp. No. 758, which is among such producer strains, has been deposited with National Institute of Bioscience and Human Technology, an international culture collection under Budapest Treaty, with the accession number of FERM BP-3420 assigned.

The pharmaceutically acceptable salt of the above Substance FR901451 includes the same kinds of salts as mentioned for the pharmaceutically acceptable salts of the compounds (2)~(3)

In addition to the foregoing substances, the following can be mentioned as examples of the substance having elastase inhibitory activity: α1-antitrypsin, SLP1 (secretory leukocyte protease inhibitor) [American Review of Respiratory Disease Vol. 147, 1993, P442–446], urinastatin, colchicine, erythromycin, clarithromycin, ICI200, 880, ONO-8046 [American Journal of Respiratory and Critical Care Medicine Vol. 153, P391–397], anti-elastase antibodies, and so forth.

For the purposes of this invention, a substance having human leukocyte elastase inhibitory activity is efficacious and can be administered for the prevention and treatment of dermal aging in general. More particularly, it can be indicated for the prevention and treatment of decreases in moistfulness, sheen, smoothness, and tonus of the skin and even increased wrinkling, or the prevention and treatment of skin flaccidity. These signs of dermal aging are suspected to arise from morphological and functional changes of the organs and tissues making up the skin, and actually, thinning of the horny layer of the epidermis and loss of oxytalan fiber in the papillary layer of the corium are noted.

The signs of dermal aging being as mentioned above, the efficacy of a substance having human leukocyte elastase inhibitory activity is particularly pronounced for the elimination or diminution of wrinkles or prevention of increased wrinkling, improvement of skin texture (fineness, handle) and amelioration of the shade of the skin (shadowy complexion).

Furthermore, said substances are efficacious for promoting neogenesis of oxytalan fiber in the region of dermal papillae and neogenesis of collagen fibrils in the dermis immediately beneath the epidermis, and for increasing the thickness of the epidermis, among others.

In addition, substances having human leukocyte elastase inhibitory activity are efficacious in various skin diseases such as scleroderma, elephantiasis, scars, steroid-induced thinning of the skin, keloids, pressure sores, wounds, refractory ulcers, psoriasis, spots, freckles, senile plaques, rough skin and pityriasis.

The following is an example of experimentation relevance to this invention.

Object of Experiment:
The therapeutic efficacy of neutrophil (leukocyte) elastase inhibitors in "dermal aging" was evaluated in hairless dogs.

Experimental Animals:

Two adult (old) experimental hairless dogs constructed by cross-breeding of a Mexican hairless dog and a beagle dog were used. Old dogs presenting with age-associated fine "wrinkles", not observed in young dogs, on the body surface were used as subject animals.

No. 8807 (10 yr old, male)
No. 8808 (10 yr old, female)

Investigational Drugs:
1) FK706·0.2%
2) FK706·0.02%
3) FR134043·0.2%
4) FR134043·0.02%
5) Polyethylene glycol (PEG) (solvent control) (PEG was used as the solvent for drugs 1~4)

Administration:

Each drug was applied in one location (a total of 5 locations) on the back (5×5 cm) of each dog. The drug was applied in a dosing volume of about 4 $\mu L/cm^2$ once daily (except on Saturdays, Sundays and holidays) for 3 months.

Evaluation Items:
1) Skin condition: Gross observation and observation with a video macroscope
2) Histology: Observation of histological changes in biopsy samples by H-E (hematoxylin-eosin) stain (general staining), van Gieson's stain (staining of collagen fiber) and Weigert's stain (staining of elastin fiber)
3) Skin thickness: Using H-E stained tissue samples, changes in thickness of the epidermis (excluding the horny layer) were studied (only the location treated with FK706 0.2%, which showed a marked improvement in skin condition, was evaluated)

Results:
1) Skin condition (remission of wrinkles)
(Gross Observation)

No. 8807: In the elimination or remission of wrinkles, the order of efficacy was FK706·0.1%>FK706·0.02%>FR134043·0.2%=FR134043·0.02%. This finding of remission was accompanied by improvements in skin texture (fineness, handle) and paralleled depigmentation of the skin (change to fair~rosy skin).

No. 8808: The order of efficacy was FK706·0.2%>FK706·0.02%>FR134043·0.2%=FR134043·0.02%.

In neither dog was found a side effect.

(Observation with a Video Macroscope)

The findings were substantially identical to the results of gross observation.

No. 8807: The order of efficacy was FK706·0.2%>FK706·0.02%>FR134043·0.2%>FR134043·0.02%.

No. 8808: The order of efficacy was FK706·0.2%=FK706·0.02%>FR134043·0.2%=FR134043 0.02%.

2) Histological Findings
van Gieson's Stain:

Neogenesis of a thin layer of collagen fiber was found across the boundary between the epidermis and dermis in the case of FK706·0.2% (Dog No. 8807)

Weigert's Strain:

Growth of elastin fibrils (suspected to be oxytalan fiber which is said to disappear as increasing age) was found across the boundary between the epidermis and dermis (Dog No. 8807).

3) Evaluation of Skin Thickness

The thickness of the epidermis was increased significantly (p<0.05 in both Dog 8807 and Dog 8808).

No. 8807: 17.0±1.9 $\mu$m→26.8±5.9 $\mu$m (mean±SD)
No. 8808: 24.6±3.6 $\mu$m→42.0±9.0 $\mu$m The composition for prophylaxis and therapy of dermal aging as provided by this invention is usually applied in the form of a preparation for external application (e.g. lotion, ointment, patch, liniment, aerosol, suspension, emulsion, etc.) or an external powder (e.g. an enzyme facial cleanser) but may also be used in the conventional pharmaceutical dosage forms such as powders, fine granules, granules, tablets, sugar-coated tablets, parenteral preparations, inhalants, microcapsules, capsules, suppositories, solutions, syrups and so on. Furthermore, it can be used in such formulations as facial cleansers, facial wash-off/emolient preparations, and bath preparations. Where necessary, a diluent or disintegrator (e.g. sucrose, lactose, starch, crystalline cellulose, low-substitution-degree hydroxypropylcellulose, synthetic aluminum silicate, etc.), a binder (e.g. cellulose, methylcellulose, hydroxypropylcellulose, hydroxypropylmethylcellulose, polypropylpyrrolidone, polyvinylpyrrolidone, gelatin, gum arabic, polyethylene glycol, etc.), a coloring agent, a sweetener and a lubricant (e.g. magnesium stearate), among others, can be additionally dispersed in such formulations.

The level of use of the composition for prophylaxis and therapy of dermal aging according to this invention depends on the species of substance used, symptoms and other factors but, generally speaking, the recommended dose of an external dosage form, in terms of the concentration of the substance having human leukocyte elastase inhibitory activity or a pharmaceutically acceptable salt thereof, can be judiciously selected from the range of about 0.001~20%, preferably about 0.01~10%.

What is claimed is:

1. A method for treatment of dermal aging comprising:

selecting a subject in need of treatment of dermal aging and externally administering to said subject a composition comprising a trifluoromethylketone derivative of the following formula or a pharmaceutically acceptable salt thereof:

wherein:
R$^1$ represents
a lower alkyl group having 1 or 2 substituents selected from the group consisting of carboxy, esterified carboxy and di-lower alkylcarbamoyl;
a phenyl(lower)alkyl group that may optionally have halogen, amino or nitro on the phenyl moiety thereof and carboxy or esterified carboxy on the alkyl moiety thereof;
a halophenyl group;
a morpholino group; or
a morpholino (lower) alkyl group;
R$^2$ and R$^3$ each independently represent a lower alkyl group;

X is either — or —NH—; and

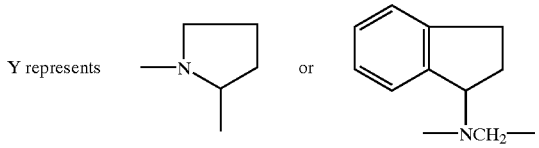

in a form and in an amount suitable for treating dermal aging.

2. A method for inducing neogenesis of collagen fiber in skin, comprising:
selecting a subject in need of the induction of the neogenesis of collagen fiber in skin, and
administering to the skin of said subject an amount of a composition comprising a trifluoromethylketone derivative of the following formula or a pharmaceutically acceptable salt thereof:

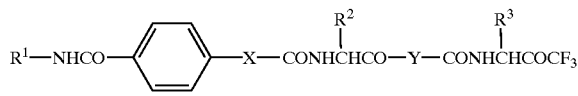

wherein:
R¹ represents
a lower alkyl group having 1 or 2 substituents selected from the group consisting of carboxy, esterified carboxy and di-lower alkylcarbamoyl;
a phenyl(lower)alkyl group that may optionally have halogen, amino or nitro on the phenyl moiety thereof and carboxy or esterified carboxy on the alkyl moiety thereof;
a halophenyl group;
a morpholino group; or
a morpholino (lower) alkyl group;
R² and R³ each independently represent a lower alkyl group;
X is either — or —NH—; and

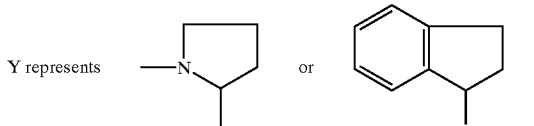

in a form and in an amount effective to induce neogenesis of collagen fiber in skin.

3. A method for inducing the growth of elastin fibrils in skin, comprising:
selecting a subject in need of the induction of the growth of elastin fibers in skin, and
externally administering to the skin of said subject a composition comprising a trifluoromethylketone derivative of the following formula or a pharmaceutically acceptable salt thereof:

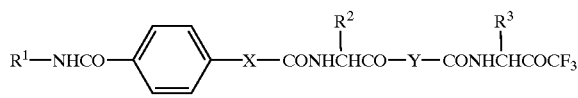

wherein:
R¹ represents
a lower alkyl group having 1 or 2 substituents selected from the group consisting of carboxy, esterified carboxy and di-lower alkylcarbamoyl;
a phenyl(lower)alkyl group that may optionally have halogen, amino or nitro on the phenyl moiety thereof and carboxy or esterified carboxy on the alkyl moiety thereof;
a halophenyl group;
a morpholino group; or
a morpholino (lower) alkyl group;
R² and R³ each independently represent a lower alkyl group;
X is either — or —NH—; and

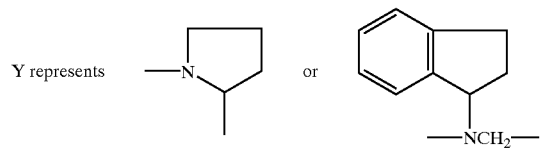

in a form and in an amount effective to induce the growth of elastin fibers.

4. A method for increasing epidermal thickness, comprising:
selecting a subject in need of an increase in epidermal thickness, and
externally administering to the skin of said subject a composition comprising a trifluoromethylketone derivative of the following formula or a pharmaceutically acceptable salt thereof:

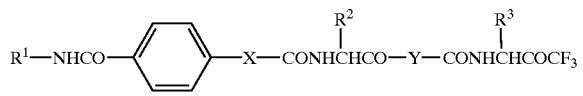

wherein:
R¹ represents
a lower alkyl group having 1 or 2 substituents selected from the group consisting of carboxy, esterified carboxy and di-lower alkylcarbamoyl;
a phenyl(lower)alkyl group that may optionally have halogen, amino or nitro on the phenyl moiety thereof and carboxy or esterified carboxy on the alkyl moiety thereof;
a halophenyl group;
a morpholino group; or
a morpholino (lower) alkyl group;
R² and R³ each independently represent a lower alkyl group;
X is either — or —NH—; and

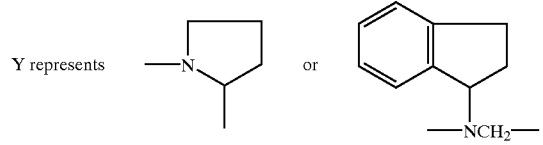

in a form and in an amount effective to increase the epidermal thickness.

5. A method for the treatment of wrinkles, comprising:
selecting a subject in need of the reduction or elimination of wrinkles, and externally administering to the skin of said subject a composition comprising a trifluoromethylketone derivative of the following formula or a pharmaceutically acceptable salt thereof:

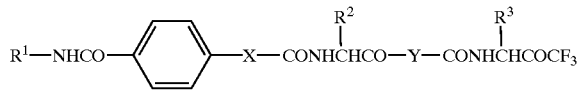

wherein:

R¹ represents a lower alkyl group having 1 or 2 substituents selected from the group consisting of carboxy, esterified carboxy and di-lower alkylcarbamoyl;

a phenyl(lower)alkyl group that may optionally have halogen, amino or nitro on the phenyl moiety thereof and carboxy or esterified carboxy on the alkyl moiety thereof;

a halophenyl group;

a morpholino group; or a morpholino (lower) alkyl group;

R² and R³ each independently represent a lower alkyl group;

X is either — or —NH—; and

Y represents 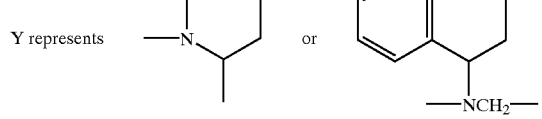

in a form and in an amount effective to reduce or eliminate wrinkles.

* * * * *